(12) United States Patent
Docimo

(10) Patent No.: US 8,133,223 B2
(45) Date of Patent: Mar. 13, 2012

(54) AUTOMATICALLY RETRACTING NEEDLE-TIP ELECTROCAUTERY DEVICE

(75) Inventor: Steven G. Docimo, Pittsburgh, PA (US)

(73) Assignee: University of Pittsburgh-Of The Commonwealth System Of Higher Education, Pittsburgh, PA (US)

( * ) Notice: Subject to any disclaimer, the term of this patent is extended or adjusted under 35 U.S.C. 154(b) by 781 days.

(21) Appl. No.: 12/175,773

(22) Filed: Jul. 18, 2008

(65) Prior Publication Data

US 2009/0024125 A1  Jan. 22, 2009

Related U.S. Application Data

(60) Provisional application No. 60/950,378, filed on Jul. 18, 2007.

(51) Int. Cl.
*A61B 18/14* (2006.01)
(52) U.S. Cl. .............. 606/45; 606/41; 606/49
(58) Field of Classification Search .......... 606/37–42, 606/45–50
See application file for complete search history.

(56) References Cited

U.S. PATENT DOCUMENTS

| | | | | |
|---|---|---|---|---|
| 4,711,239 A | * | 12/1987 | Sorochenko et al. | 606/48 |
| 5,222,953 A | * | 6/1993 | Dowlatshahi | 606/15 |
| 6,010,476 A | * | 1/2000 | Saadat | 604/22 |
| 6,221,071 B1 | * | 4/2001 | Sherry et al. | 606/41 |
| 6,287,297 B1 | * | 9/2001 | Woodruff et al. | 606/7 |
| 6,497,704 B2 | * | 12/2002 | Ein-Gal | 606/41 |
| 6,569,161 B2 | | 5/2003 | Zappala | |
| 6,923,807 B2 | * | 8/2005 | Ryan et al. | 606/41 |
| 6,974,455 B2 | * | 12/2005 | Garabedian et al. | 606/41 |
| 2007/0112343 A1 | * | 5/2007 | Mische et al. | 606/41 |

* cited by examiner

*Primary Examiner* — Michael Peffley
(74) *Attorney, Agent, or Firm* — Reed Smith LLP

(57) ABSTRACT

Medical devices that useful during electrocauterization procedures. The present invention encompasses a needle-tipped electrocautery device in which the needle tip is housed within the body of the device when the device is not in use. When an extension mechanism on the electrocautery stylus is activated, the tip is exposed and may be used for surgical procedures. The mechanism may be either mechanically driven or electronically driven. The present invention thereby dramatically reduces the risk of injury or infection by inadvertent pricks from an electrocautery tool.

8 Claims, 2 Drawing Sheets

AUTOMATICALLY RETRACTING NEEDLE-TIP ELECTROCAUTERY DEVICE

CROSS-REFERENCE TO RELATED APPLICATION

This application claims the benefit under 35 U.S.C. §119 (e) of the earlier filing date of U.S. Provisional Application Ser. No. 60/950,378 filed on Jul. 18, 2007.

BACKGROUND OF THE INVENTION

1. Field of the Invention

The present invention relates generally to surgical tools and more specifically to hand-held electrocautery devices.

2. Description of the Background

Electrocautery is the process of damaging tissue using electrical current that is widely used in modern surgery. Electrocautery may be performed to cut through soft tissue or to stop bleeding from small blood vessels. Electrocautery surgical devices are typically hand-held units that include a metal tip through which the electrical current is applied to the tissue.

An electrocautery stylus is a variety of electrocautery device that is commonly employed in surgery procedures. The metal tip of the stylus may be either sharp or dull. The advantage of a sharp, needle-like tip is precision in cutting and cauterization. Unfortunately, the sharp tip represents a hazard on the surgical field carrying with it the risk of needle-stick transmission of blood-borne pathogens.

Other surgical tools with sharp ends have covers that are employed to shield the sharp end of the tool from the surgical room personnel. Some of those covers take the form of separate pieces that may be detached from the surgical tool before use. In other cases, the cover is integrated with the device and must be retracted manually prior to each use of the device. For electrocautery styluses, such solutions are unsuitable because the stylus is used repeatedly during surgery and the repetitive step of removal or retraction of the cover would impede the tool's regular use.

Thus, there has been a long-standing need in the surgical art area for a needle-tipped electrocautery device that protects medical practitioners from accidental needle pricks while at the same time maintaining the utility of the device for the surgeon.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein.

SUMMARY OF THE INVENTION

Figure 1:
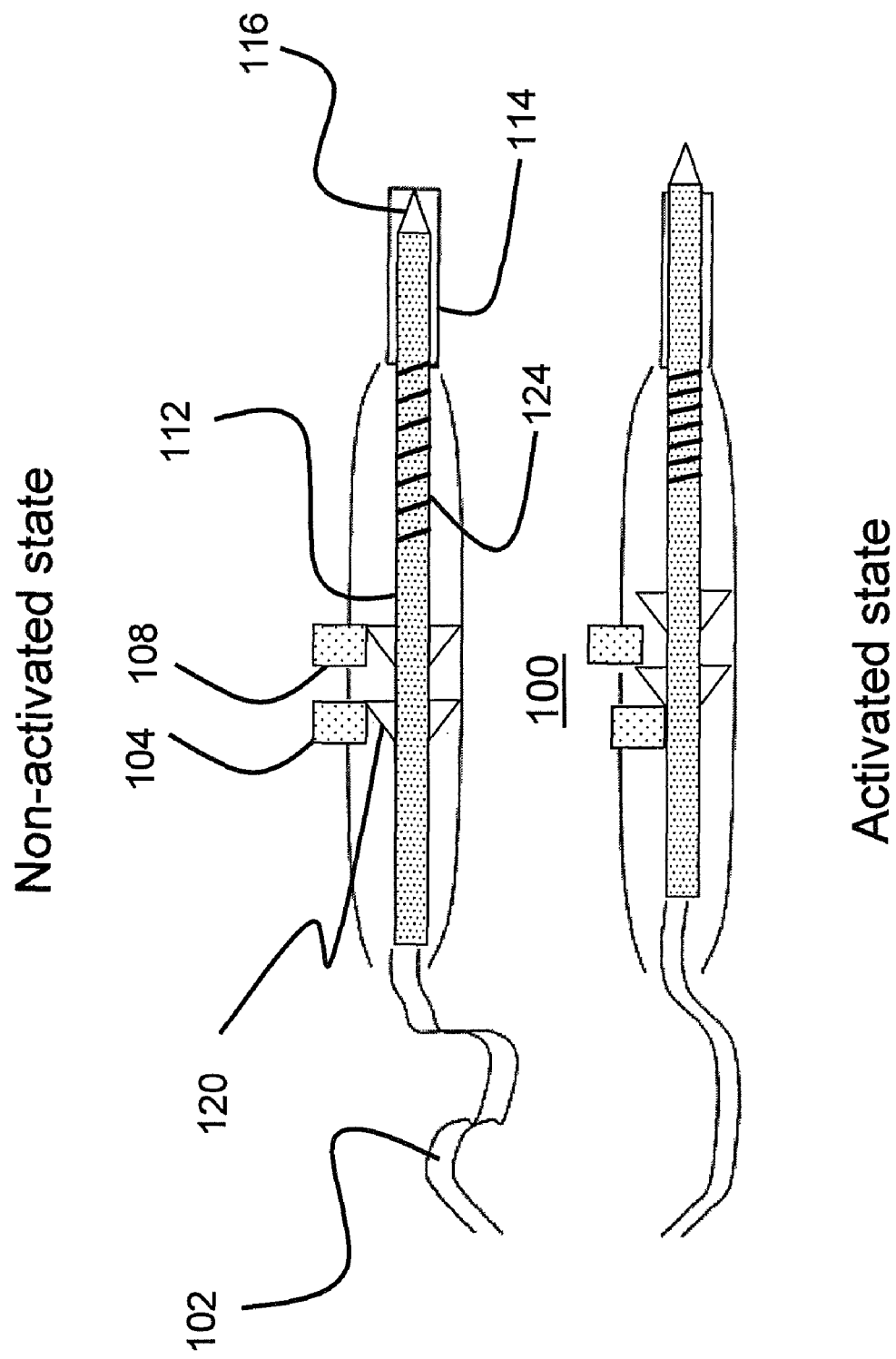
FIG. 1 shows an embodiment of the present invention that is mechanically driven.

The present invention encompasses medical devices that are useful during electrocauterization procedures. In presently preferred embodiments, the device is a needle-tipped electrocautery device in which the needle tip is housed within the body of the device when the device is not in use. When an extension mechanism on the electrocautery stylus is activated, the tip is exposed and may be used for surgical procedures. The mechanism may be either mechanically driven or electronically driven. The present invention thereby dramatically reduces the risk of injury or infection by inadvertent pricks from an electrocautery tool.

DETAILED DESCRIPTION OF THE INVENTION

It is to be understood that the figures and descriptions of the present invention have been simplified to illustrate elements that are relevant for a clear understanding of the invention, while eliminating, for purposes of clarity, other elements that may be well known. The detailed description will be provided hereinbelow with reference to the attached drawings.

The present invention preferably encompasses apparatuses for use in surgery. Presently preferred embodiments of the present invention include a hand-held electrocautery stylus with a retractable needle tip. When not in use, the devices of the present invention have the electrocautery needle tip covered to prevent accidental injury. When employed by the medical practitioner, the present invention allows for a mechanism to be engaged which exposes the needle tip, thus allowing for its surgical use.

In certain presently preferred embodiments, the present invention is a modification on the design of hand-held electrocautery devices. As such, all of the circuitry used in implementing electrocautery devices may be employed within the context of the present invention. Such circuitry would be well known to those of skill in the art. Typically, electrocautery devices of the prior art possess two actuating buttons—one for administering an amount of current sufficient for coagulation and one for administering an amount of current sufficient for cutting tissue. When the buttons are depressed, the appropriate current is delivered through a stylus tip to the tissue. After the device is removed from its packaging, the stylus tip is constantly exposed to the surgical field.

The present invention preferably includes an electrocautery device with a needle tip that is shielded within a sheath in the unused state. To retain the standard functionality, the present invention also employs two actuating buttons similar to those used in the prior art electrocautery devices. In certain presently preferred embodiments, pressing either of the actuating buttons results in exposure of the needle tip. That may be accomplished either through advancement of the needle out of a sheath, or by retraction of the sheath to expose the needle. Following use of the device, needle tip is once again covered until the device is re-used by the surgeon.

The movement of either the sheath or the needle may be accomplished in a variety of ways. For example, movement of the needle may be achieved mechanically as depicted schematically in FIG. 1. The embodiment shown in FIG. 1 omits the well-known components that make up the electrocauterization circuitry, which may be supplied power through the power line shown 102. In certain presently preferred embodiments, either one of the actuating buttons 104 108 may interact with a spring-loaded extension 112 of the sheath or needle 116. In the embodiment shown in FIG. 1, an extension 112 of the needle 116 is shown. When either actuating button 104 108 is depressed, it physically may engage a ramped element 120 located on the extension. When the buttons 104 108 engage the ramped element 120, the extension 112 is forced forward thereby extending the needle tip 116 from the device 100 beyond the sheath 114. When not in use, an internal spring 124 may force the needle 116 to retract into the device 100.

In other embodiments, the button may engage ramped elements oriented in the opposite direction thereby retracting a sheath assembly and exposing the needle tip of the device. When not in use, the internal springs force the sheath forward thereby covering the needle tip of the device.

In addition to the embodiment shown in FIG. 1, one of skill in the art may envision numerous other mechanical means of extending the cauterization needle from the housing of the device. For example, a ratcheted mechanism may be employed in which a button, which is distinct from the cauterization actuating buttons, drives the electrocauterization needle from the housing of the device. Once exposed, the needle is locked in the extended position by a ratcheting-type mechanism. When the surgeon is finished using the electrocautery device, the button may be depressed again, thereby activating the ratchet and allowing the needle to be retracted into the body of the device. Other mechanisms well known to those of skill in the art may be employed within the context of the present invention to effect a mechanical exposure of the stylus tip.

Figure 2:
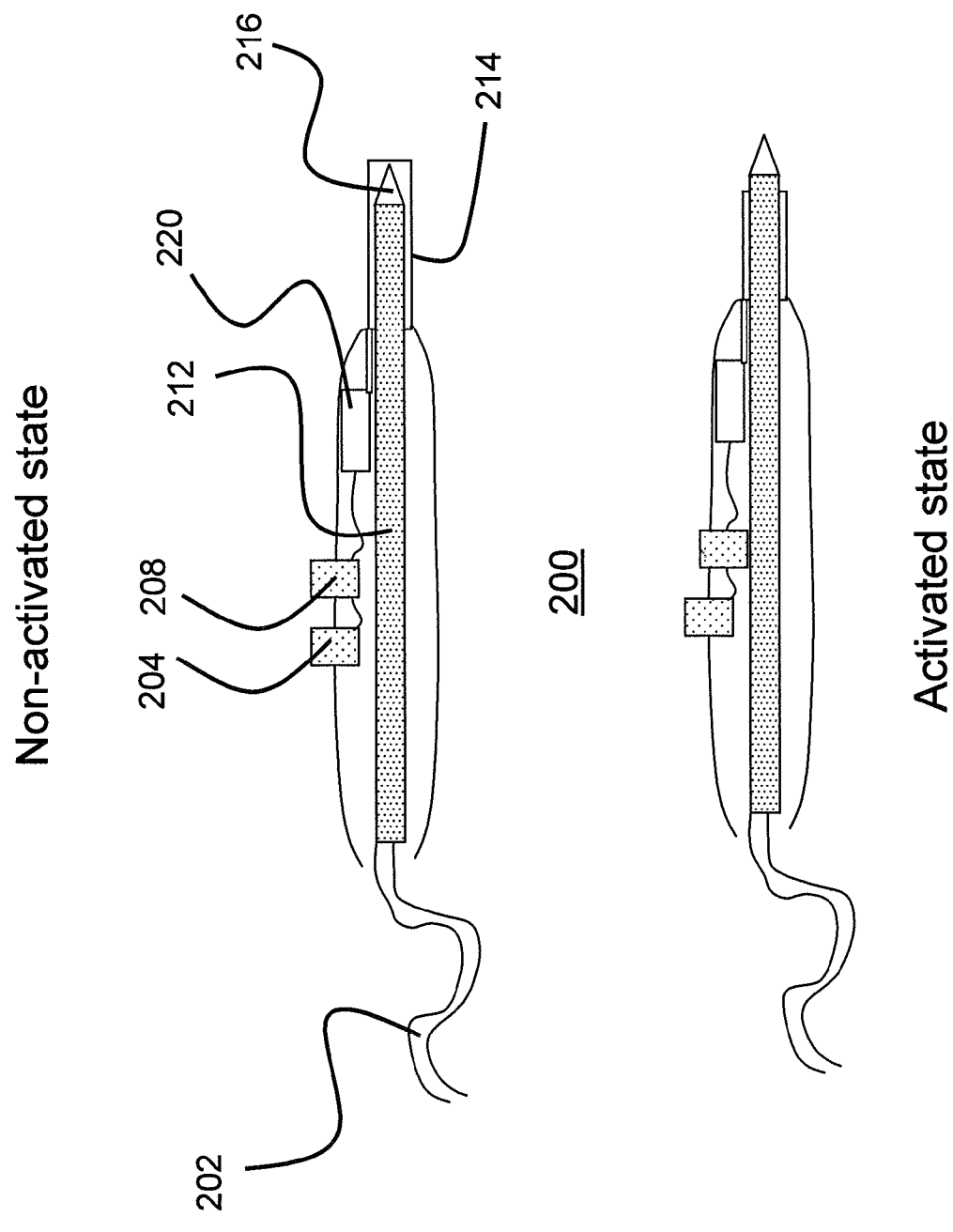
FIG. 2 displays an embodiment of the present invention that is electronically driven.

In other implementations, the retraction of the sheath or extension of the needle tip could be accomplished electronically by a motor 220 housed within the electrocautery device 200 as shown schematically in FIG. 2. The embodiment shown in FIG. 2 omits the well-known components that make up the electrocauterization circuitry, which may be supplied power through the power line shown 202. In such implementations, when either button 204 208 is depressed, a motor 220 is engaged. In the embodiment shown in FIG. 2, the motor 220 drives the electrocautery needle 216 from the device 200 beyond the sheath 214. In alternative embodiments, the sheath may be similarly retracted, thereby exposing the needle. One of skill in the art will recognize many motors or motorized components that could be used within the context of the present invention. Examples include linear actuators, solenoids, piezo-driven motors, worm gears, or other common DC motors. Any implementation employing motorized components would preferably engage those motorized components only when the actuator buttons are depressed. Therefore, the overall functionality of the prior art electrocautery device would be retained allowing surgical practitioners to maintain their high level of skill and practice.

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the drawings and the descriptions herein are proffered only to facilitate comprehension of the invention and should not be construed to limit the scope thereof.

I claim:

1. A device for use in electrocautery, comprising:
   a housing;
   circuitry adapted to accomplish tissue cutting and cauterization;
   a needle tip, wherein said needle tip is electrically coupled to said circuitry;
   at least two actuating buttons, wherein said actuating buttons are adapted to engage said circuitry; and
   a sheath, wherein said sheath is adapted to conceal said needle tip when said device is not in use; and
   a mechanical component for exposing said needle tip comprising a shaft comprising ramped elements, wherein said ramped elements are adapted for selective engagement by said at least one actuator button.

2. The device of claim 1, wherein said shaft is adapted to selectively engage said needle tip.

3. The device of claim 2, wherein said mechanical component is adapted to drive said shaft forward thereby exposing said needle tip when at least one of said actuating buttons is activated.

4. The device of claim 1, wherein said shaft is adapted to selectively engage said sheath.

5. The device of claim 4, wherein said mechanical component is adapted to retract said sheath thereby exposing said needle tip when at least one of said actuating buttons is activated.

6. The device of claim 1, further comprising springs located inside of said housing.

7. The device of claim 6, wherein said springs maintain said sheath in an extended position when said device is not in use.

8. The device of claim 6, wherein said springs maintain said needle tip in a concealed position when said device is not in use.

* * * * *